United States Patent
Lee et al.

(10) Patent No.: US 8,846,986 B2
(45) Date of Patent: Sep. 30, 2014

(54) WATER SEPARATION FROM CRUDE ALCOHOL PRODUCT

(75) Inventors: David Lee, Seabrook, TX (US); Adam Orosco, League City, TX (US); Lincoln Sarager, Houston, TX (US); R. Jay Warner, Houston, TX (US); Trinity Horton, Houston, TX (US); Radmila Jevtic, Pasadena, TX (US); Victor J. Johnston, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 526 days.

(21) Appl. No.: 13/094,641

(22) Filed: Apr. 26, 2011

(65) Prior Publication Data

US 2012/0273339 A1    Nov. 1, 2012

(51) Int. Cl.
| | | |
|---|---|---|
| *C07C 29/149* | (2006.01) | |
| *C07C 29/76* | (2006.01) | |
| *C07C 29/80* | (2006.01) | |
| *C07C 31/08* | (2006.01) | |
| *C07C 67/08* | (2006.01) | |

(52) U.S. Cl.
CPC .............. *C07C 29/149* (2013.01); *C07C 29/76* (2013.01); *C07C 29/80* (2013.01); *C07C 67/08* (2013.01); *C07C 31/08* (2013.01)
USPC ............ 568/884; 568/885; 568/916; 568/917

(58) Field of Classification Search
CPC ........ C07C 31/08; C07C 29/80; C07C 29/76; C07C 29/149
USPC ......... 568/840, 876, 880, 881, 883, 884, 885, 568/890, 894, 916, 917; 203/19; 435/161
See application file for complete search history.

(56) References Cited

U.S. PATENT DOCUMENTS

| | | | |
|---|---|---|---|
| 1,939,116 | A | 12/1933 | Fuchs |
| 2,649,407 | A | 8/1953 | Harrison |
| 2,702,783 | A | 2/1955 | Harrison |
| 2,744,939 | A | 5/1956 | Kennel |
| 2,859,241 | A | 11/1958 | Schnizer |
| 2,882,244 | A | 4/1959 | Milton |
| 3,130,007 | A | 4/1964 | Breck |
| 3,408,267 | A | 10/1968 | Miller |
| 3,445,345 | A | 5/1969 | Adam |
| 3,478,112 | A | 11/1969 | Adam |

(Continued)

FOREIGN PATENT DOCUMENTS

| | | |
|---|---|---|
| EP | 0104197 | 4/1984 |
| EP | 0137749 | 4/1985 |

(Continued)

OTHER PUBLICATIONS

International Search Report and Written Opinion mailed Sep. 19, 2012 in corresponding International Application No. PCT/US2011/059882.

(Continued)

*Primary Examiner* — Jafar Parsa
*Assistant Examiner* — Amy C Bonaparte

(57) ABSTRACT

Recovery of alcohol, in particular ethanol, from a crude product obtained from the hydrogenation of acetic acid using various combinations of membranes and/or distillation columns.

20 Claims, 2 Drawing Sheets

(56) References Cited

U.S. PATENT DOCUMENTS

| | | |
|---|---|---|
| 3,769,329 A | 10/1973 | Paulik et al. |
| 3,772,380 A | 11/1973 | Paulik et al. |
| 3,990,952 A | 11/1976 | Katzen |
| 4,275,228 A | 6/1981 | Gruffaz |
| 4,306,942 A | 12/1981 | Brush |
| 4,317,918 A | 3/1982 | Takano |
| 4,319,058 A | 3/1982 | Kulprathipanja |
| 4,370,491 A | 1/1983 | Bott et al. |
| 4,379,028 A | 4/1983 | Berg |
| 4,395,576 A | 7/1983 | Kwantes |
| 4,398,039 A | 8/1983 | Pesa |
| 4,421,939 A | 12/1983 | Kiff |
| 4,422,903 A | 12/1983 | Messick |
| 4,454,358 A | 6/1984 | Kummer |
| 4,456,775 A | 6/1984 | Travers et al. |
| 4,465,854 A | 8/1984 | Pond |
| 4,471,136 A | 9/1984 | Larkins |
| 4,480,115 A | 10/1984 | McGinnis |
| 4,492,808 A | 1/1985 | Hagen |
| 4,497,967 A | 2/1985 | Wan |
| 4,517,391 A | 5/1985 | Schuster et al. |
| 4,520,213 A | 5/1985 | Victor |
| 4,541,897 A | 9/1985 | Sommer |
| 4,569,726 A | 2/1986 | Berg |
| 4,611,085 A | 9/1986 | Kitson |
| 4,626,321 A | 12/1986 | Grethlein |
| 4,628,130 A | 12/1986 | Bournonville et al. |
| 4,678,543 A | 7/1987 | Houben |
| 4,692,218 A | 9/1987 | Houben |
| 4,774,365 A | 9/1988 | Chen |
| 4,777,303 A | 10/1988 | Kitson |
| 4,804,791 A | 2/1989 | Kitson |
| 4,826,795 A | 5/1989 | Kitson et al. |
| 4,842,693 A | 6/1989 | Wheldon |
| 4,961,826 A | 10/1990 | Grethlein |
| 4,985,572 A | 1/1991 | Kitson |
| 4,990,655 A | 2/1991 | Kitson |
| 4,994,608 A | 2/1991 | Torrence |
| 5,001,259 A | 3/1991 | Smith |
| 5,026,908 A | 6/1991 | Smith |
| 5,035,776 A | 7/1991 | Knapp |
| 5,047,592 A | 9/1991 | Carpenter |
| 5,061,671 A | 10/1991 | Kitson |
| 5,070,016 A | 12/1991 | Hallberg |
| 5,124,004 A | 6/1992 | Grethlein |
| 5,144,068 A | 9/1992 | Smith |
| 5,149,680 A | 9/1992 | Kitson |
| 5,185,308 A | 2/1993 | Bartley et al. |
| 5,185,481 A | 2/1993 | Muto |
| 5,215,902 A | 6/1993 | Tedder |
| 5,227,141 A | 7/1993 | Kim |
| 5,233,099 A | 8/1993 | Tabata |
| 5,237,108 A | 8/1993 | Marraccini |
| 5,250,271 A | 10/1993 | Horizoe |
| 5,348,625 A | 9/1994 | Berg |
| 5,415,741 A | 5/1995 | Berg |
| 5,437,770 A | 8/1995 | Berg |
| 5,445,716 A | 8/1995 | Berg |
| 5,449,440 A | 9/1995 | Rescalli |
| 5,502,248 A | 3/1996 | Funk et al. |
| 5,527,969 A | 6/1996 | Kaufhold et al. |
| 5,565,068 A | 10/1996 | Parker et al. |
| RE35,377 E | 11/1996 | Steinberg |
| 5,599,976 A | 2/1997 | Scates |
| 5,762,765 A | 6/1998 | Berg |
| 5,770,770 A | 6/1998 | Kim et al. |
| 5,800,681 A | 9/1998 | Berg |
| 5,821,111 A | 10/1998 | Grady |
| 5,861,530 A | 1/1999 | Atkins et al. |
| 5,993,610 A | 11/1999 | Berg |
| 5,998,658 A | 12/1999 | Wu et al. |
| 6,093,845 A | 7/2000 | Van Acker et al. |
| 6,121,498 A | 9/2000 | Tustin |
| 6,143,930 A | 11/2000 | Singh |
| 6,232,352 B1 | 5/2001 | Vidalin |
| 6,294,703 B1 | 9/2001 | Hara |
| 6,375,807 B1 | 4/2002 | Nieuwoudt |
| 6,472,555 B2 | 10/2002 | Choudary et al. |
| 6,509,180 B1 | 1/2003 | Verser |
| 6,627,770 B1 | 9/2003 | Cheung |
| 6,657,078 B2 | 12/2003 | Scates |
| 6,685,754 B2 | 2/2004 | Kindig |
| 6,693,213 B1 | 2/2004 | Kolena |
| 6,723,886 B2 | 4/2004 | Allison |
| 6,755,975 B2 | 6/2004 | Vane |
| 6,906,228 B2 | 6/2005 | Fischer |
| 6,927,048 B2 | 8/2005 | Verser |
| 7,005,541 B2 | 2/2006 | Cheung |
| 7,074,063 B1 | 7/2006 | Bailey |
| 7,091,155 B2 | 8/2006 | Inui et al. |
| 7,115,772 B2 | 10/2006 | Picard |
| 7,208,624 B2 | 4/2007 | Scates |
| 7,297,236 B1 | 11/2007 | Vander Griend |
| 7,321,052 B2 * | 1/2008 | Miller et al. .................. 560/231 |
| 7,351,559 B2 | 4/2008 | Verser |
| 7,399,892 B2 | 7/2008 | Rix |
| 7,507,562 B2 | 3/2009 | Verser |
| 7,553,397 B1 | 6/2009 | Colley |
| 7,572,353 B1 | 8/2009 | Vander Griend |
| 7,594,981 B2 | 9/2009 | Ikeda |
| 7,601,865 B2 | 10/2009 | Verser |
| 7,608,744 B1 | 10/2009 | Johnston |
| 7,652,167 B2 | 1/2010 | Miller et al. |
| 7,667,068 B2 | 2/2010 | Miller et al. |
| 7,682,812 B2 | 3/2010 | Verser |
| 7,718,039 B2 | 5/2010 | Dirkzwager et al. |
| 7,732,173 B2 | 6/2010 | Mairal |
| 7,744,727 B2 | 6/2010 | Blum |
| 7,842,844 B2 | 11/2010 | Atkins |
| 7,863,489 B2 | 1/2011 | Johnston |
| 7,884,253 B2 | 2/2011 | Stites |
| 7,888,082 B2 | 2/2011 | Verser |
| 2003/0135069 A1 | 7/2003 | Fujita et al. |
| 2004/0152915 A1 | 8/2004 | Fujita et al. |
| 2004/0242917 A1 | 12/2004 | Inui et al. |
| 2006/0019360 A1 | 1/2006 | Verser |
| 2006/0224013 A1 | 10/2006 | Inui et al. |
| 2006/0252956 A1 | 11/2006 | Miller et al. |
| 2007/0138083 A1 | 6/2007 | Aizawa |
| 2007/0270511 A1 | 11/2007 | Melnichuk |
| 2008/0135396 A1 | 6/2008 | Blum |
| 2008/0193989 A1 | 8/2008 | Verser |
| 2008/0207959 A1 * | 8/2008 | Plante et al. .................. 568/916 |
| 2009/0014313 A1 | 1/2009 | Lee |
| 2009/0023192 A1 | 1/2009 | Verser |
| 2009/0069609 A1 | 3/2009 | Kharas |
| 2009/0081749 A1 | 3/2009 | Verser |
| 2009/0166172 A1 | 7/2009 | Casey |
| 2009/0216051 A1 * | 8/2009 | Brown et al. .................. 568/915 |
| 2009/0281354 A1 | 11/2009 | Mariansky |
| 2009/0299092 A1 | 12/2009 | Beavis et al. |
| 2009/0318573 A1 | 12/2009 | Stites |
| 2010/0029980 A1 | 2/2010 | Johnston |
| 2010/0029995 A1 | 2/2010 | Johnston |
| 2010/0030001 A1 | 2/2010 | Chen |
| 2010/0030002 A1 | 2/2010 | Johnston |
| 2010/0121114 A1 | 5/2010 | Weiner |
| 2010/0130775 A1 | 5/2010 | Voss et al. |
| 2010/0185021 A1 | 7/2010 | Ross et al. |
| 2010/0197485 A1 | 8/2010 | Johnston |
| 2011/0082322 A1 | 4/2011 | Jevtic et al. |
| 2012/0010437 A1 | 1/2012 | Jevtic et al. |
| 2012/0010438 A1 | 1/2012 | Lee et al. |
| 2012/0010439 A1 | 1/2012 | Jevtic et al. |
| 2012/0010440 A1 | 1/2012 | Sarager et al. |
| 2012/0277481 A1 | 11/2012 | Warner et al. |

FOREIGN PATENT DOCUMENTS

| | | |
|---|---|---|
| EP | 0167300 | 1/1986 |
| EP | 0175558 | 3/1986 |
| EP | 0285420 | 10/1988 |
| EP | 0400904 | 5/1990 |
| EP | 0372847 | 6/1990 |

(56) References Cited

FOREIGN PATENT DOCUMENTS

| | | |
|---|---|---|
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 1-268654 | 10/1989 |
| JP | 4-193304 | 7/1992 |
| JP | 6-116182 | 4/1994 |
| WO | WO 82/03854 | 11/1982 |
| WO | 8303409 | 10/1983 |
| WO | WO 98/25876 | 6/1998 |
| WO | 2008135192 | 11/2008 |
| WO | 2009009322 | 1/2009 |
| WO | 2009009323 | 1/2009 |
| WO | WO 2009/009320 | 1/2009 |
| WO | 2009048335 | 4/2009 |
| WO | WO 2009/063176 A1 * | 5/2009 ............ C07C 29/149 |
| WO | WO 2009/105860 | 9/2009 |
| WO | 2010055285 | 5/2010 |
| WO | WO 2011/097227 | 8/2011 |
| WO | WO 2011/140460 | 11/2011 |
| WO | WO 2012/006219 | 1/2012 |
| WO | WO 2012/006228 | 1/2012 |

OTHER PUBLICATIONS

Marian Simo et al., "Adsorption/Desorption of Water and Ethanol on 3A Zeolite in Near-Adiabatic Fixed Bed", Industrial & Engineering Chemistry Research, vol. 48, No. 20, Sep. 25, 2009, XP 55027304, pp. 9247-9260.

Tracy J. Benson et al., "Cellulose Based Adsorbent Materials for the Dehydration of Ethanol Using Thermal Swing Adsorption", Adsorption, Kluwer Academic Publishers, BO, vol. 11, No. 1, Jul. 1, 2005, XP 019203738.

Hidetoshi Kita et al., "Synthesis of a zeolite NaA membrane for pervaporation of water/organic liquid mixtures", Journal of Materials Science Letters, vol. 14.

International Search Report and Written Opinion mailed Jun. 28, 2012 in corresponding International Application No. PCT/US2011/060017.

N. Calvar et al., "Esterification of acetic acid with ethanol: Reaction kinetics and operation in a packed bed reactive distillation column", Chemical Engineering and Processing, vol. 46, No. 12, Oct. 9, 2007, XP 022290064, pp. 1317-1323.

Yang et al., Process of Ethanol Synthesis through esterification of acetic acid and economic analysis, No. 4, 2011, 15 Pages.

International Search Report an Written Opinion mailed Feb. 23, 2012 in corresponding International Application No. PCT/US2011/042646.

Written Opinion mailed Jul. 9, 2012 in corresponding International Application No. PCT/US2011/042646.

International Search Report and Written Opinion mailed Jul. 11, 2012 in corresponding International Application No. PCT/US2012/035182.

International Search Report and Written Opinion mailed Jul. 11, 2012 in corresponding International Application No. PCT/US2012/035203.

Alcala, et al., (2005). Experimental and DFT studies of the conversion of ethanol and acetic acid on PtSn-based catalysts, Journal of Physical Chemistry, 109(6), 2074-2085.

Amit M. Goda et al., DFT modeling of selective reduction of acetic acid to acetaldehyde on Pt-based bimetallic catalysts, 20th NAM, Houston, TX, Jun. 17-22, 2007 available online at http://www.nacatsoc.org/20nam/abstracts/O-S9-18.pdf.

Baker, et al., "Membrane separation systems: recent developments and future directions," 1991, pp. 151-169.

Burkhanov, et al., "Palladium-Based Alloy Membranes for Separation of High Purity Hydrogen from Hydrogen-Containing Gas Mixtures," Platinum Metals Rev., 2011, 55, (1), pp. 3-12.

English language abstract for EP 0 137 749 A2.

English language abstract for EP 0 456 647 A1.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Hilmen, Separation of Azeotropic Mixtures: Tools for Analysis and Studies on Batch Distillation Operation (Nov. 2000) p. 17-20.

Huang et al., "Low-Energy Distillation-Membrane Separation Process," vol. 49, Jan. 3, 2010, pp. 3760-3768.

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Perry, et al., "Perry's Chemical Engineer's Handbook," 7th ed., 1997, pp. 22-37 to 22-69.

Rachmady, Acetic Acid Reduction by H2 on Bimetallic Pt" Fe Catalysts, Journal of Catalysis 209, 87-98 (Apr. 1, 2002), Elsevier Science (USA).

Santori et al. (2000). Hydrogenation of carbonylic compounds on Pt/SiO2 catalysts modified with SnBu4, Studies in Surface Science and Catalysis, 130, 2063-2068.

ZeaChem, Inc., Technology Overview, Lakewood, Colorado www.zeachem.com, 2008.

Zheng, et al. (2007). Preparation and catalytic properties of a bimetallic Sn—Pt complex in the supercages of NaY zeolite by use of surface organometallic chemistry, Applied Organometallic Chemistry, 21(10), 836-840.

International Preliminary Report on Patentability for PCT/US2011/059882 mailed Nov. 7, 2013.

Response to Final Office Action for U.S. Appl. No. 13/094,488, filed Dec. 20, 2013.

Response to Final Office Action for U.S. Appl. No. 13/094,610, filed Oct. 18, 2013.

Supplemental Response to Final Office Action for U.S. Appl. No. 13/094,688, filed Dec. 3, 2013.

Response to Final Office Action for U.S. Appl. No. 13/094,688, filed Nov. 25, 2013.

Response to Final Office Action for U.S. Appl. No. 13/094,661, filed Nov. 25, 2013.

Response to Final Office Action for U.S. Appl. No. 13/094,537, filed Dec. 27, 2013.

* cited by examiner

US 8,846,986 B2

WATER SEPARATION FROM CRUDE ALCOHOL PRODUCT

FIELD OF THE INVENTION

The present invention relates generally to processes for producing alcohol and, in particular, to removing water from a crude ethanol product.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acetic acid remains in the crude ethanol product, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

Ethanol recovery systems for other types of ethanol production processes are also known. For example, U.S. Pub. No. 2008/0207959 describes a process for separating water from ethanol using a gas separation membrane unit. The gas separation membrane unit may be used to remove water from a fermentation broth that has been partially dewatered, for example by one or more of a distillation column or molecular sieves. Additional systems employing membranes and distillation columns are described in U.S. Pat. Nos. 7,732,173; 7,594,981; and 4,774,365, the entireties of which are incorporated herein by reference. See also Huang, et al, "Low-Energy Distillation-Membrane Separation Process," *Ind. Eng. Chem. Res.*, Vol. 40 (2010), pg. 3760-68, the entirety of which is incorporated herein by reference.

The need remains for improved processes for recovering ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol, comprising hydrogenating acetic acid from an acetic acid feed stream in a reactor to form a crude ethanol product comprising ethanol, acetic acid, and water; removing a majority of the water from the crude ethanol product to form a water stream and a dry crude product, wherein the dry crude product comprises less than 5 wt. % water; and recovering ethanol from the dry crude product.

In a second embodiment, the present invention is directed to a process for producing ethanol, comprising hydrogenating acetic acid from an acetic acid feed stream in a reactor to form a crude ethanol product comprising ethanol, acetic acid, and water; removing a majority of the water in the crude ethanol product to form a water stream and a dry crude product; feeding the dry crude product to a reactive distillation column; and withdrawing a distillate comprising ethyl acetate and acetaldehyde, and a residue comprising ethanol.

In a third embodiment, the present invention is directed to a process for producing ethanol, comprising hydrogenating acetic acid from an acetic acid feed stream in a reactor to form a crude ethanol product comprising ethanol, acetic acid, and water; removing a majority of the water in the crude ethanol product to form a water stream and a dry crude product; separating at least a portion of the dry crude product in a first column to yield a first residue comprising acetic acid and a first distillate comprising ethanol and ethyl acetate; and separating at least a portion of the first distillate in a second column to yield a second distillate comprising ethyl acetate and a second residue comprising ethanol.

In a fourth embodiment, the present invention is directed to a process for producing ethanol, comprising providing a crude ethanol product comprising ethanol, acetic acid, ethyl acetate, and water; removing a majority of the water in the crude ethanol product to form a water stream and a dry crude product, wherein the dry crude product comprises less than 5 wt. % water; and recovering ethanol from the dry crude product.

BRIEF DESCRIPTION OF DRAWINGS

The invention may be more completely understood in consideration of the following detailed description of various embodiments of the invention in connection with the accompanying drawings, wherein like numerals designate similar parts.

DETAILED DESCRIPTION OF THE INVENTION

Introduction

Figure 1:
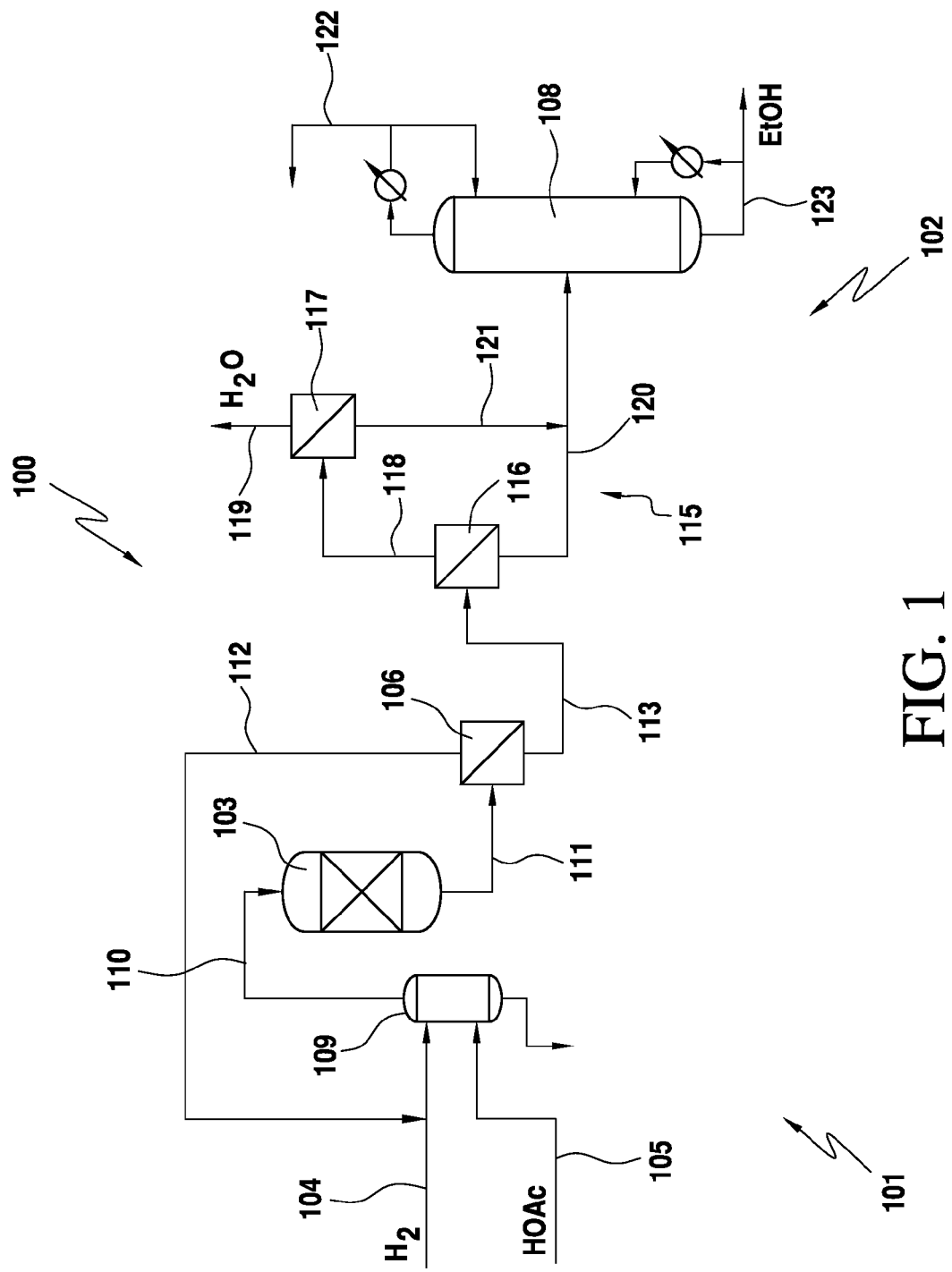
FIG. 1 is a schematic diagram of an ethanol production system having a combined distillation and membrane separation system in accordance with one embodiment of the present invention.

The present invention relates to processes for recovering ethanol produced by hydrogenating acetic acid in the presence of a catalyst. The hydrogenation reaction produces a crude ethanol product that comprises ethanol, water, ethyl acetate, unreacted acetic acid, and other impurities. The concentration of some of these compounds in the reaction mixture is largely a factor of catalyst composition and process conditions. In the hydrogenation of acetic acid, water is coproduced with ethanol in about a 1:1 molar ratio. Thus, producing additional ethanol also results in the production of additional water.

The processes of the invention involve removing a substantial portion of the water from the crude ethanol product. Preferably, a majority of the water from the crude ethanol product is removed before further separation. In one embodiment, the process removes at least 90% of the water from the crude ethanol product, e.g., at least 95% of the water or at least 97% of the water. In terms of ranges, the process may remove from 90% to 99.9% of the water that was contained in the crude ethanol product, e.g., from 95% to 99% or from 97% to 99%. Preferably, the water is removed before any appreciable amount of acetic acid and/or organics, e.g., ethyl acetate or acetaldehyde, are removed from the crude ethanol product. Removing water as an initial separation step beneficially results in an energy savings over other separation schemes for removing water.

In the water removal step, the water may be separated from a crude ethanol product with an adsorption unit, one or more membranes, molecular sieves, or a combination thereof. Preferably, the majority of the water in the initial water separation step is not removed using a distillation column. Suitable adsorption units include pressure swing adsorption (PSA) units and thermal swing adsorption (TSA) units. The adsorption units may comprise molecular sieves, such as aluminosilicate compounds. The use of adsorption units and/or membranes provides a low energy alternative to distillation columns for separating water from ethanol. In addition, adsorption units and/or membranes may be able to break the ethanol-water azeotrope to remove more water than a typical distillation column.

If an adsorption unit is employed for water removal, the adsorption unit may employ a suitable adsorption agent such as zeolite 3A or 4A. In one preferred embodiment, the adsorption unit comprises a pressure swing adsorption (PSA) unit that is operated at a temperature from 30° C. to 160° C., e.g., from 80° C. to 140° C., and a pressure of from 0.01 kPa to 550 kPa, e.g., from 1 kPa to 150 kPa. The PSA unit may comprise from two to five beds. In one embodiment, the crude ethanol product is fed to a PSA to produce a water stream and a dry crude product stream.

In some embodiments, the crude ethanol product is fed to a membrane or an array of membranes. The water preferably permeates across the membranes producing a dry crude product as a retentate stream. In this context, it should be appreciated that the term "dry" is used relative to the stream entering the membrane system as the retentate stream may comprise a minor amount of water. Suitable membranes include acid resistant membranes that have increased water permeability, i.e., high selectivities for permeating water. In one embodiment, the membrane may be a pervaporation membrane. The membrane may comprise a polymeric membrane, for example, comprising polyimide hollow fibers. Alternatively, the membrane may be a zeolite membrane or a hybrid membrane with both organic and inorganic components. The membrane or membranes preferably comprise one or more pervaporation membranes. Suitable membranes include shell and tube membrane modules having one or more porous material elements therein. Non-porous material elements may also be included. The material elements may comprise a polymeric element such as polyvinyl alcohol, cellulose esters, and perfluoropolymers. Membranes that may be employed in embodiments of the present invention include those described in Baker, et al., "Membrane separation systems: recent developments and future directions," (1991) pages 151-169, and Perry et al., "Perry's Chemical Engineer's Handbook," $7^{th}$ ed. (1997), pages 22-37 to 22-69, the entire contents and disclosures of which are hereby incorporated by reference.

It should be noted that one or more membranes may be used in series or in parallel in order to achieve the desirable purity of the final ethanol product. In addition, it should be noted that either the permeate and/or the retentate stream may pass through additional membranes. Also a stream may be recycled through the same membrane to remove undesirable materials. For example, if it is desirable to obtain crude ethanol product with reduced amount of water, the initial crude ethanol product stream may be fed through a first water permeable membrane. Then, the retentate stream may be fed through a second water permeable membrane to yield a second retentate stream. The second permeate stream may be recycled and combined with the initial crude ethanol product stream to capture additional ethanol.

As indicated above, the dry crude product may comprise a minor amount of water. For example, the dry crude product may comprise less than 5 wt. % water, e.g., less than 4 wt. % water or less than 3 wt. % water. In terms of ranges, the dry crude product may comprise from 0.05 to 5 wt. % water, e.g., from 0.1 to 4 wt. % or from 0.3 to 3 wt. %. In one embodiment, the water concentration of the dry crude product is less than the azeotropic amount of water for the crude ethanol product.

Since the water stream that is removed from the crude ethanol product may be purged from the reaction system, it is preferred that the water stream comprises substantially no ethanol, e.g., less than 5000 wppm ethanol, or less than 500 wppm ethanol or less than 50 wppm ethanol. In order to ensure that a minimal amount of ethanol, if any at all, is removed from the system with the water stream, it may be desirable to use highly selective membranes, such as zeolite membranes. Highly selective membranes that minimize the amount of organics, including ethanol, that pass through the membrane in the permeate stream are preferred. In addition to water, the water stream may comprise acetic acid, and/or other organics, e.g., ethyl acetate or acetaldehyde, which would not be expected to significantly impact the amount of ethanol that is removed in the water stream. In some embodiments, when an array of membranes is used or a portion of the water stream is fed to another column, the membrane may be less selective for water and the water stream may contain up to 30 wt. % ethanol.

The dry crude product may be further processed to recover ethanol. Depending on conversion and selectivity in the reactor, the dry crude product also may comprise acetic acid and organics in addition to ethanol. One or more distillation columns may be used to remove these components. In addition, the remaining water may also be removed from the dry crude product and/or a derived ethanol stream, using an adsorption unit, one or more membranes, molecular sieves, extractive column distillations, or a combination thereof. Suitable adsorption units include pressure swing adsorption (PSA) units and thermal swing adsorption (TSA) units.

Hydrogenation Process

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259 and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature.

Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa (about 1.5 to 435 psi), e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 wt. % to 99.9 wt. %, e.g., from 78 wt. % to 97 wt. %, or from 80 wt. % to 95 wt. %. In preferred embodiments that utilize a modified support, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain NorPro. The Saint-Gobain NorPro SS61138 silica exhibits the following properties: contains approximately 95 wt. % high surface area silica; a surface area of about 250 m$^2$/g; a median pore diameter of about 12 nm; average pore volume of about 1.0 cm$^3$/g as measured by mercury intrusion porosimetry and a packing density of about 0.352 g/cm$^3$ (22 lb/ft$^3$).

A preferred silica/alumina support material is KA-160 silica spheres from Sud Chemie having a nominal diameter of about 5 mm, a density of about 0.562 g/ml, an absorptivity of about 0.583 g $H_2O$/g support, a surface area of about 160 to 175 m$^2$/g, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 15 tons of ethanol per hour, preferably at least 30 tons of ethanol per hour. In terms of ranges, for large scale industrial production of ethanol, the process of the present invention may produce 15 to 160 tons of ethanol per hour, e.g., 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 35 wt. % water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | 0 to 90 | 0 to 50 | 15 to 70 | 20 to 70 |
| Water | 5 to 40 | 5 to 30 | 10 to 30 | 10 to 26 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product comprises acetic acid in an amount less than 20 wt. %, e.g., less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

Ethanol Production

Figure 2:
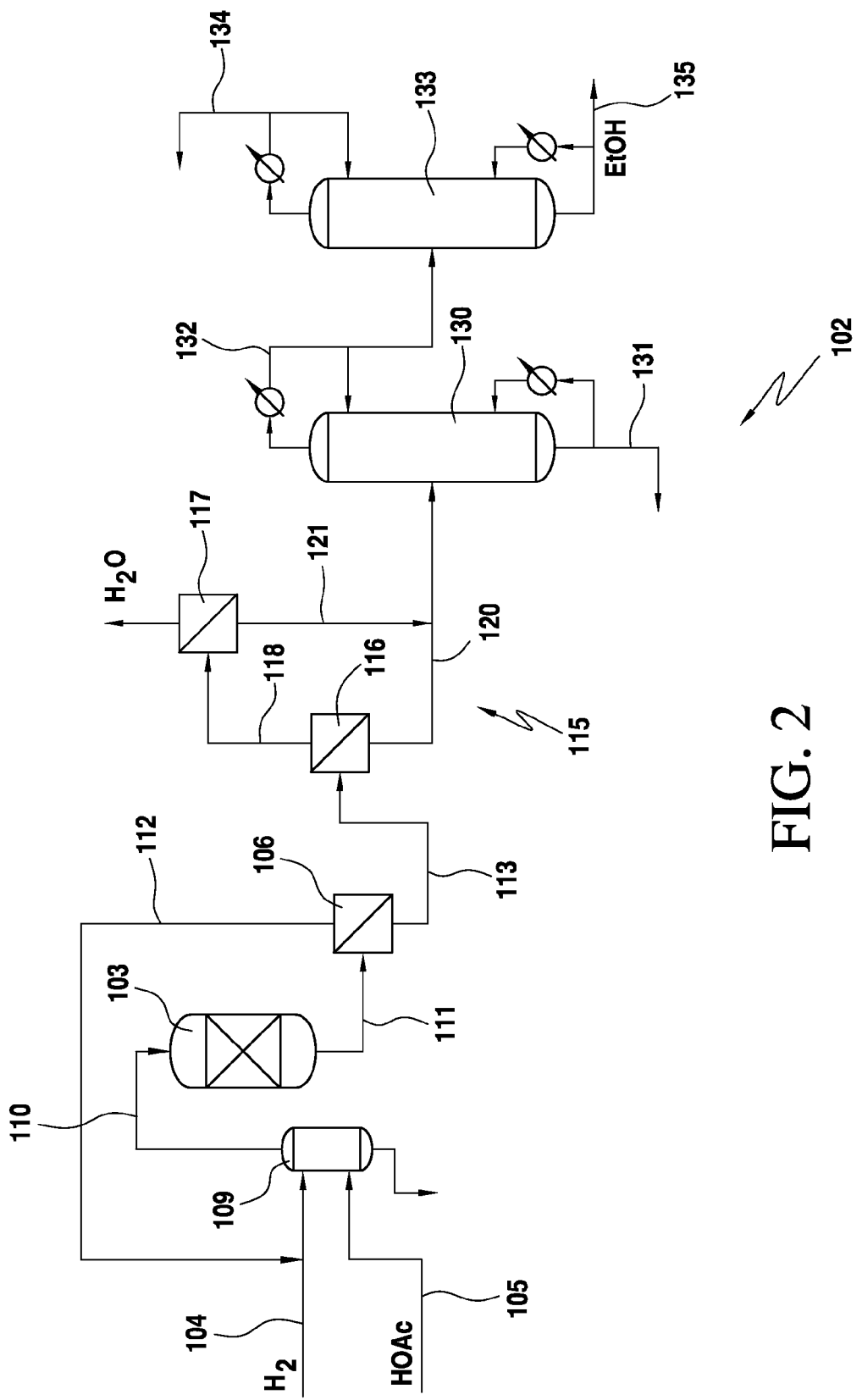
FIG. 2 is a schematic diagram of an ethanol production system having a combined distillation and membrane separation system with two distillation columns in accordance with one embodiment of the present invention.

Exemplary ethanol recovery systems in accordance with embodiments of the present invention are shown in FIGS. 1 and 2. Each hydrogenation system 100 provides a suitable hydrogenation reactor and a process for separating ethanol from the crude reaction mixture according to an embodiment of the invention. System 100 comprises reaction zone 101 in which hydrogen and acetic acid are fed to a vaporizer 109 via lines 104 and 105, respectively, to create a vapor feed stream in line 110 that is directed to reactor 103. In one embodiment, lines 104 and 105 may be combined and jointly fed to the vaporizer 109. The temperature of the vapor feed stream in line 110 is preferably from 100° C. to 350° C., e.g., from 120° C. to 310° C. or from 150° C. to 300° C. Any feed that is not vaporized is removed from vaporizer 109 and may be recycled or discarded. In addition, although line 110 is shown as being directed to the top of reactor 103, line 110 may be directed to the side, upper portion, or bottom of reactor 103. Further modifications and additional components to reaction zone 101 and separation zone 102 are described below.

Reactor 103 contains the catalyst that is used in the hydrogenation of the carboxylic acid, preferably acetic acid. In one embodiment, one or more guard beds (not shown) may be used upstream of the reactor to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol product stream is withdrawn, preferably continuously, from reactor 103 via line 111.

As shown in FIG. 1, ethanol is recovered from the crude ethanol product in line 111 using separation zone 102. The crude ethanol product in line 111 passes through one or more membranes 106 to separate hydrogen and/or other non-condensable gases therefrom. Hydrogen and/or other non-condensable gases may be returned to the reaction zone 101 via permeate stream 112. Gases in permeate stream 112 may be combined with the hydrogen feed 104 and co-fed to vaporizer 109. The retentate stream 113 is fed to a water separation zone 115. Preferably, retentate stream 113 is in the vapor phase and may be compressed before entering water separation zone 115. In an embodiment, membrane 106 is a polymer based membrane operate at a maximum temperature of 100° C. and at a pressure of greater than 500 kPa, e.g., greater than 700 kPa. In another embodiment, membrane 106 is a palladium-based membrane, such as palladium-based alloy with copper, yttrium, ruthenium, indium, lead, and/or rare earth metals, that has a high selectivity for hydrogen. Suitable palladium-based membranes are described in Burkhanov, et al., "Palladium-Based Alloy Membranes for Separation of High Purity Hydrogen from Hydrogen-Containing Gas Mixtures," *Platinum Metals Rev.*, 2011, 55, (1), 3-12, the entirety of which is incorporated by reference. Efficient hydrogen separation palladium-based membranes generally have high hydrogen permeability, low expansion when saturated with hydrogen, good corrosion resistance and high plasticity and strength during operation at temperatures of 300 to 700° C. Because the crude ethanol product may contain unreacted acid, membrane 106 should tolerate acidic conditions of about pH 3 to 4.

Optionally, the crude ethanol product stream in line 111 is condensed and fed to a separator (not shown), which, in turn, provides a vapor stream comprising non-condensable gases, and a liquid stream comprising ethanol, water, acetic acid and other organics. The separator may be in the form of a flasher or a knockout pot. The separator may operate at a temperature from 20° C. to 250° C., e.g., from 30° C. to 225° C. or from 60° C. to 200° C. and at a pressure from 50 kPa to 2000 kPa, e.g., from 75 kPa to 1500 kPa, or from 100 kPa to 1000 kPa. The vapor stream exiting the separator may comprise hydrogen and hydrocarbons, which may be purged and/or returned to reaction zone 101. The liquid stream may be fed to the water separation zone 115. In this optional embodiment, water separation zone 115 may operate in the liquid phase.

Water Separation

Water separation zone 115 may comprise one or more adsorption units, membranes, molecular sieves, or a combination thereof. In one preferred embodiment, water separation zone 115 may comprise one or more membranes. Water may be removed from a liquid crude ethanol product using pervaporation membranes or a vapor crude ethanol product through vapor permeation. The zeolite membrane are hydrophilic and are suitable for separating water from organic mixtures due to high selectivities for water. Commercially available zeolite membrane include NaA type zeolite membrane developed by Mitsui Engineering & Shipbuilding Co. Those membranes may also tolerate acidity up to pH about 3 to 4. Other suitable polymer membranes which are more acid tolerant include perfluoro membranes developed by Membrane Technologies and Research.

In FIGS. 1 and 2, water separation zone 115 comprises an array of membranes 116 and 117. Preferably, both membranes 116 and 117 are acid resistant and have high selectivities for water. Retentate stream 113 may pass through a compressor (not shown), which supplies a driving force, passes through first membrane 116. An intermediate water stream 118 permeates across first membrane 116 and is fed to a second membrane 117. Similarly, intermediate water stream 118 passes through a compressor (not shown), which supplies a driving force, and over second membrane 117 to form a second permeate stream as shown by water stream 119 and a second retentate stream 121. In this manner, the first membrane 116 removes a portion of the water and the second membrane 117 recovers ethanol and other organics that may have undesirably permeated through first membrane 116. Water stream 119 may be purged from the system as necessary or recycled to another step in the process if desired. Additional membranes, in series and/or in parallel, may be added to the array as necessary to further enhance water removal. Retentate streams 120 and 121 from membranes 116 and 117, respectively, may be combined to form a dry crude product that may be further processed to recover ethanol. In some embodiments, it may be desired to process each retentate stream 120 and 121 separately. The membrane array configuration shown in water separation zone 115 of FIG. 1 is but one of many possible array configurations that may be employed in the present invention. In another array configuration, not shown, water separation zone 115 includes two (or more) membranes in series. In this aspect, stream 113 may be directed to a first membrane where a first amount of water is removed in a first permeate. The resulting retentate is then sent to a second membrane where an additional amount of water is removed in a second permeate and forming a second retentate that may be further processed with additional membranes in a similar manner and/or sent to an ethanol recovery system. Additional membranes, in series and/or in parallel, may be added to the array as necessary to further enhance water removal. Optionally, depending on the composition of the permeate or retentate streams, a portion of these streams may be recycled back, directly or indirectly, to reaction zone 101. For example if the permeate stream comprises a high concentration of acetic acid, it may be beneficial to return the permeate stream to the reactor via vaporizer. Whichever membrane array configuration is employed, in preferred embodiments, the water separation system removes at least 90%, at least 95% or at least 97%, of the water from the original stream, e.g., stream 113, that is sent to the water separation system.

Exemplary components of water stream 119 and dry crude product (combination of retentate streams 120 and 121) are provided in Table 2 below. It should be understood that these streams may also contain additional components, not listed in Table 2.

TABLE 2

WATER SEPARATION

|  | Conc. (wt. %) | Conc. (wt. %) | Conc. (wt. %) |
|---|---|---|---|
| Dry crude product |  |  |  |
| Ethanol | 5 to 80 | 15 to 75 | 25 to 65 |
| Water | <5 | 0.001 to 3 | 0.01 to 1 |
| Acetic Acid | <95 | 0.001 to 75 | 0.01 to 25 |
| Ethyl Acetate | <35 | 0.001 to 25 | 0.01 to 15 |
| Acetaldehyde | <15 | 0.001 to 10 | 0.01 to 5 |
| Acetal | <10 | 0.001 to 6 | 0.01 to 4 |
| Acetone | <5 | 0.001 to 3 | 0.01 to 2 |
| Water Stream |  |  |  |
| Acetic Acid | <10 | 0.001 to 5 | 0.01 to 2 |
| Water | 70 to 100 | 80 to 99.5 | 85 to 99 |
| Ethanol | <10 | 0.001 to 5 | 0.01 to 2 |

The amounts indicated as less than (<) in the tables throughout present application are preferably not present and if present may be present in trace amounts or in amounts greater than 0.0001 wt. %.

Ethanol Recovery

In one embodiment, the dry crude product may be sent to a reactive distillation column 108 where unreacted acetic acid may be esterified with ethanol to form ethyl acetate. Reactive distillation column 108 produces a distillate in line 122 comprising ethyl acetate and acetaldehyde, and an ethanol residue in line 123. In one embodiment, column 108 is a tray column having from 5 to 70 trays, e.g., from 15 to 50 trays or from 20 to 45 trays.

In some embodiments, reactive distillation column 108 may comprise a reaction zone that contains a catalyst, such as an acidic catalyst. Suitable catalysts include, without limitation, alkyl sulfonic acids and aromatic sulfonic acids, e.g., methane sulfonic acid, benzene sulfonic acid and p-toluene sulfonic acid. Alternatively, sulfuric acid or heteropoly acids can be used within the scope of the invention. A variety of homogeneous or heterogeneous acids may also be employed within the scope of this invention.

A majority of the acetic acid in the dry crude product may be consumed in reactive distillation column 108, e.g., at least 50% of the acetic acid, and more preferably at least 90%. In reacting the acetic acid, a portion of the ethanol is also consumed. Preferably less than 25% of the ethanol in the dry crude product is consumed, and more preferably less than 5%. The residue in line 123 may comprise any remaining amounts of acetic acid, but preferably is substantially free of acetic acid, e.g., containing less than 5000 wppm acetic acid, and more preferably less than 500 wppm acetic acid. Optionally, residue in line 123 may be neutralized to remove residual acetic acid. The reaction may produce additional amounts of ethyl acetate and/or water than is present in the dry crude product. A majority of the ethyl acetate preferably is withdrawn from column 108 in the distillate in line 122 and the water, if any, is withdrawn in the residue in line 123 with the ethanol.

Residue in line 123 may contain some amounts of residual water. Depending on the desired ethanol product, it may be desired to further dry the residue in line 123. Residual water removal may be accomplished, for example, using one or more adsorption units, membranes, molecular sieves, extractive distillation, or a combination thereof. Suitable adsorption units include pressure swing adsorption units and thermal swing adsorption units.

The distillate in line 122, which comprises ethyl acetate and/or acetaldehyde, preferably is refluxed as shown in FIG. 1, for example, at a reflux ratio of from 1:30 to 30:1, e.g., from 1:5 to 5:1 or from 1:3 to 3:1. In one aspect, not shown, the distillate or a portion thereof may be returned to reactor 103. In some embodiments, it may be advantageous to return a portion of distillate to reactor 103. The ethyl acetate and/or acetaldehyde in the distillate may be further reacted in hydrogenation reactor 103 or in an secondary reactor. The outflow from the secondary reactor may be fed to reactor 103 to produce additional ethanol or to a distillation column to recover additional ethanol.

In other embodiments, the acetic acid may be separated from the dry crude product using an acid separation column 130, as shown in FIG. 2. Depending on the acetic acid conversion, it may be preferable to recover the acetic acid from the dry crude product.

In the embodiment shown in FIG. 2, dry crude product is introduced in a first column 130, which is also known as an "acid separation column" Dry crude product is introduced to the lower part of first column 130, e.g., lower half or lower third. In column 130, unreacted acetic acid, any remaining water, and other heavy components, if present, are removed from the dry crude product and are withdrawn, preferably continuously, as residue in line 131. In some embodiments, it may be preferable to withdraw a majority of the water in the residue. Acid separation column 130 also forms an overhead distillate, which is withdrawn in line 132, and which may be condensed and refluxed, for example, at a ratio of from 10:1 to 1:10, e.g., from 3:1 to 1:3 or from 1:2 to 2:1.

When column 130 is operated under 170 kPa pressure, the temperature of the residue exiting in line 131 preferably is from 120° C. to 150° C., e.g., from 128° C. to 142° C. or from 136° C. to 143° C. The temperature of the distillate exiting in line 132 preferably is from 85° C. to 95° C., e.g., from 85° C. to 91° C. or from 87° C. to 95° C. In some embodiments, the pressure of acid separation column 130 may range from 0.1 kPa to 510 kPa, e.g., from 1 kPa to 475 kPa or from 1 kPa to 375 kPa. Exemplary components for the distillate and residue compositions for the column 130 are provided in Table 3, below. It should be understood that the distillate and residue may also contain other components, not listed in Table 3.

TABLE 3

ACID SEPARATION COLUMN 130

|  | Conc. (wt. %) | Conc. (wt. %) | Conc. (wt. %) |
| --- | --- | --- | --- |
| First Distillate |  |  |  |
| Ethyl Acetate | <55 | 1 to 50 | 3 to 45 |
| Acetaldehyde | <10 | 0.1 to 5 | 0.3 to 3 |
| Water | <15 | 0.1 to 10 | 0.3 to 7 |
| Ethanol | 35 to 100 | 40 to 98 | 45 to 96 |
| Acetal | <10 | 0.1 to 5 | 0.2 to 3 |
| First Residue |  |  |  |
| Water | <40 | 0.001 to 30 | 0.001 to 25 |
| Ethanol | <40 | 0.01 to 30 | 0.01 to 25 |
| Ethyl Acetate | <2 | 0.001 to 1 | 0.01 to 0.5 |
| Acetic Acid | 50 to 100 | 60 to 99.5 | 70 to 99 |

Some species, such as acetals, may decompose in column 108 such that very low amounts, or even no detectable amounts, of acetals remain in the distillate or residue. In addition, an equilibrium reaction between acetic acid and ethanol or between ethyl acetate and water may occur in the crude ethanol product after it exits reactor 103. Depending on the concentration of acetic acid in the crude ethanol product, this equilibrium may be driven toward formation of ethyl acetate. This equilibrium may be regulated using the residence time and/or temperature of crude ethanol product.

Depending on the amount of water and acetic acid contained in the residue of column 130, line 131 may be treated in one or more of the following processes. The following are exemplary processes for further treating first residue and it should be understood that any of the following may be used regardless of acetic acid concentration. When the residue comprises a majority of acetic acid, e.g., greater than 70 wt. %, the residue may be recycled to the reactor without any separation of the water. In one embodiment, the residue may be separated into an acetic acid stream and a water stream when the residue comprises a majority of acetic acid, e.g., greater than 50 wt. %. Acetic acid may also be recovered in some embodiments from the first residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to reactor 103. The resulting water stream may be used as an extractive agent or to hydrolyze an ester-containing stream in a hydrolysis unit.

In other embodiments, for example where residue in line 113 comprises less than 50 wt. % acetic acid, possible options include one or more of: (i) returning a portion of the residue to reactor 103, (ii) neutralizing the acetic acid, (iii) reacting the acetic acid with an alcohol, or (iv) disposing of the residue in a waste water treatment facility.

Optionally, crude ethanol product in line 111 or the dry crude product may be further fed to an esterification reactor, hydrolysis reactor, hydrogenolysis reactor, or combination thereof. An esterification reactor may be used to consume acetic acid present in the crude ethanol product to further reduce the amount of acetic acid that would otherwise need to be removed. Hydrolysis may be used to convert ethyl acetate into acetic acid (which may be recycled to reaction zone 101) and ethanol, while hydrogenolysis may be used to convert ethyl acetate in the crude ethanol product to ethanol.

The distillate in line 132 preferably comprises ethanol and optionally ethyl acetate, acetaldehyde, and water. The final ethanol product may be derived from the distillate in line 132. In one embodiment, the weight ratio of water in the residue to the water in the distillate is greater than 1:1, e.g., greater than 2:1 or greater than 4:1. In addition, the weight ratio of acetic acid in the residue to acetic acid in the distillate is optionally greater than 10:1, e.g., greater than 15:1 or greater than 20:1. Preferably, the distillate in line 132 is substantially free of acetic acid and may contain, if any, only trace amounts of acetic acid.

As shown in FIG. 2, there is also provided a light ends column 133, also referred to as a second column, that removes ethyl acetate and acetaldehyde from the first distillate in line 132. In this embodiment, column 133 produces a second distillate in line 134 comprising ethyl acetate and acetaldehyde, and a second residue in line 135 comprising ethanol and possibly some water.

First distillate in line 132 is introduced to the second column 133 preferably in the top part of column, e.g., top half or top third. Column 133 may be a tray column or packed column In one embodiment, column 133 is a tray column having from 5 to 70 trays, e.g., from 15 to 50 trays or from 20 to 45 trays. As one example, when a 30 tray column is utilized in a column without water extraction, line 132 is introduced preferably at tray 2.

Optionally, the light ends column may be an extractive distillation column. Suitable extractive agents may include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof. In another aspect, the extractive agent may be an aqueous stream comprising water. If the extraction agent comprises water, the water may be obtained from an external source or from an internal return/recycle line from one or more of the other columns, such as from a portion of the water stream 119. Generally, the extractive agent is fed above the entry point of distillate in line 132. When extractive agents are used, a suitable recovery system, such as a further distillation column, may be used to remove the extractive agent and recycle the extractive agent.

Although the temperature and pressure of second column 133 may vary, when at about 20 kPa to 70 kPa, the temperature of the second residue exiting in line 135 preferably is from 30° C. to 75° C., e.g., from 35° C. to 70° C. or from 40° C. to 65° C. The temperature of the second distillate exiting in line 134 preferably is from 20° C. to 55° C., e.g., from 25° C. to 50° C. or from 30° C. to 45° C. Second column 133 may operate at a reduced pressure, near or at vacuum conditions, to further favor separation of ethyl acetate and ethanol. In other embodiments, the pressure of column 133 may range from 0.1 kPa to 510 kPa, e.g., from 1 kPa to 475 kPa or from 1 kPa to 375 kPa. Exemplary components for the second distillate and second residue compositions for second column 133 are provided in Table 4, below. It should be understood that the second distillate and second residue may also contain other components, not listed in Table 4.

TABLE 4

LIGHT ENDS COLUMN 133

|  | Conc. (wt. %) | Conc. (wt. %) | Conc. (wt. %) |
|---|---|---|---|
| Second Distillate |  |  |  |
| Ethyl Acetate | 10 to 90 | 25 to 90 | 50 to 90 |
| Acetaldehyde | 1 to 45 | 1 to 40 | 1 to 35 |
| Water | <25 | 1 to 20 | 4 to 16 |
| Ethanol | <30 | 0.001 to 15 | 0.01 to 5 |
| Acetal | <5 | 0.001 to 2 | 0.01 to 1 |
| Second Residue |  |  |  |
| Water | <20 | 0.001 to 15 | 0.01 to 10 |
| Ethanol | 20 to 75 | 30 to 70 | 40 to 70 |
| Ethyl Acetate | <3 | 0.001 to 2 | 0.001 to 0.5 |
| Acetic Acid | 0 to 0.5 | 0.001 to 0.3 | 0.01 to 0.2 |

The weight ratio of ethanol in the second residue to ethanol in the second distillate preferably is at least 2:1, e.g., at least 5:1, at least 8:1, at least 10:1 or at least 15:1. The weight ratio of ethyl acetate in the second residue to ethyl acetate in the second distillate preferably is less than 0.4:1, e.g., less than 0.2:1 or less than 0.1:1. It should be understood that when an extractive agent is used, that the composition of the residue would also include the extractive agent.

Depending on the intended ethanol application, it may be desirable to remove water from the second residue in line 135. In some embodiments, removing substantially all of the water produces an anhydrous ethanol product suitable for fuel applications. Water may be removed from the second residue in line 135 using any of several different separation techniques. Particularly preferred techniques include the use of a distillation column, one or more membranes, one or more adsorption units or a combination thereof.

The second distillate in line 134, which comprises ethyl acetate and/or acetaldehyde, preferably is refluxed as shown in FIG. 2, for example, at a reflux ratio of from 1:30 to 30:1, e.g., from 1:5 to 5:1 or from 1:3 to 3:1. In one aspect, not shown, the distillate or a portion thereof may be returned to reactor 103. In some embodiments, it may be advantageous to return a portion of distillate to reactor 103. The ethyl acetate and/or acetaldehyde in the distillate may be further reacted in hydrogenation reactor 103 or in an additional separate reactor before returning to reactor 103 to produce additional ethanol.

Any of columns described with embodiments of the present invention may comprise any distillation column capable of separation and/or purification. Each column preferably comprises a tray column having from 1 to 150 trays, e.g., from 10 to 100, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, that the temperature at a given location in an operating distillation column is dependent on the composition of the material at that location and the pressure of column. In addition, feed rates may vary depending on the size of the production process and, if described, may be generically referred to in terms of feed weight ratios.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and flasher are shown, additional reactors, flashers, condensers, heating elements, and other components may be used in embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The finished ethanol composition obtained by the processes of the present invention preferably comprises from 75 to 100 wt. % ethanol, e.g., from 80 to 99.5 wt. % or from 85 to 99.5 wt. % ethanol, based on the total weight of the finished ethanol composition. Exemplary finished ethanol compositional ranges are provided below in Table 5.

TABLE 5

FINISHED ETHANOL COMPOSITIONS

| Component | Conc. (wt. %) | Conc. (wt. %) | Conc. (wt. %) |
|---|---|---|---|
| Ethanol | 75 to 97 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be higher than indicated in Table 5, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. No. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated by reference.

In order that the invention disclosed herein may be more efficiently understood, an example is provided below. It should be understood that this example is for illustrative purposes only and is not to be construed as limiting the invention in any manner.

EXAMPLE 1

Acetic acid was hydrogenated in the presence of a catalyst with a conversion rate of 90.0%. Crude ethanol product stream having 54.5 wt. % ethanol, 25.2 wt. % water, 10.0 wt. % acetic acid, 9.0 wt. % of ethyl acetate and 0.6 wt. % acetaldehyde was fed through an array of membranes with a selectivity for water. The permeate stream contained 100 wt. % water and the retentate stream contained 72.9 wt. % ethanol, 13.4 wt. % acetic acid, 12.0 wt. % ethyl acetate, 0.8 wt. % acetaldehyde, 0.8 wt. % DEA, and less than 0.01 wt. % water. The retentate stream was introduced to an acid separation column to separate into a distillate stream and a residue stream. The distillate stream contained 84.1 wt. % ethanol, 13.9 wt. % ethyl acetate, 1.0 wt. % acetaldehyde, 0.9 wt. % DEA, and 0.1 wt. % water. The residue stream comprised 99.1 wt. % acetic acid, 0.5 wt. % ethanol, and 0.4 wt. % DEA.

While the invention has been described in detail, modifications within the spirit and scope of the invention will be readily apparent to those of skill in the art. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol, comprising the steps of:
    hydrogenating acetic acid from an acetic acid feed stream in a reactor to form a crude ethanol product comprising ethanol, acetic acid, and water;
    removing a majority of the water from the crude ethanol product using an adsorption unit, one or more membranes, molecular sieves, or a combination thereof to form a water stream and a dry crude product comprising ethanol and acetic acid, wherein the dry crude product comprises less than 5 wt. % water; and
    feeding the dry crude product directly to one or more distillation columns to recover ethanol therefrom.

2. The process of claim 1, wherein at least 90% of the water from the crude ethanol is removed from the crude ethanol product.

3. The process of claim 1, wherein from 90% to 99.9% of the water from the crude ethanol is removed from the crude ethanol product.

4. The process of claim 1, wherein the water stream comprises less than 5000 wppm ethanol.

5. The process of claim 1, wherein the adsorption unit is selected from the group of pressure swing adsorption units and thermal swing adsorption units.

6. The process of claim 1, wherein the one or more membranes are acid resistant and have high selectivities for permeating water.

7. The process of claim 1, wherein water is removed from the crude ethanol product before a majority of the acetic acid is removed from the crude ethanol product.

8. The process of claim 1, wherein dry crude product comprises 25 to 65 wt. % ethanol, less than 25 wt. % acetic acid, less than 15 wt. % ethyl acetate, and less than 5 wt. % water.

9. The process of claim 1, further comprising
   feeding the dry crude product to a reactive distillation column; and
   withdrawing a distillate comprising ethyl acetate and acetaldehyde, and a residue comprising ethanol.

10. The process of claim 9, wherein the reactive distillation column comprises an acidic catalyst.

11. The process of claim 9, wherein the residue further comprises water, and further comprising reducing the water content of the residue to yield an ethanol product stream with reduced water content.

12. The process of claim 9, wherein at least a portion of the distillate is returned to the reactor.

13. The process of claim 9, wherein the residue comprises less than 5000 wppm acetic acid.

14. The process of claim 9, wherein the acetic acid conversion in the hydrogenation reaction is greater than 90%.

15. The process of claim 1, further comprising
   separating at least a portion of the dry crude product in a first column to yield a first residue comprising acetic acid and a first distillate comprising ethanol and ethyl acetate; and
   separating at least a portion of the first distillate in a second column to yield a second distillate comprising ethyl acetate and a second residue comprising ethanol.

16. The process of claim 15, wherein the second residue further comprises water, and further comprising reducing the water content of the second residue to yield an ethanol product stream with reduced water content.

17. A process for producing ethanol, comprising the steps of:
   hydrogenating acetic acid from an acetic acid feed stream in a reactor to form a crude ethanol product comprising ethanol, acetic acid, ethyl acetate, acetaldehyde and water;
   removing a majority of the water in the crude ethanol product using an adsorption unit, one or more membranes, molecular sieves, or a combination thereof to form a water stream and a dry crude product comprising ethanol, acetic acid, ethyl acetate, and acetaldehyde;
   feeding the dry crude product directly to a reactive distillation column; and
   withdrawing a distillate comprising ethyl acetate and acetaldehyde, and a residue comprising ethanol.

18. A process for producing ethanol, comprising the steps of:
   hydrogenating acetic acid from an acetic acid feed stream in a reactor to form a crude ethanol product comprising ethanol, acetic acid, ethyl acetate, and water;
   removing a majority of the water in the crude ethanol product using an adsorption unit, one or more membranes, molecular sieves, or a combination thereof to form a water stream and a dry crude product comprising ethanol, acetic acid, and ethyl acetate;
   separating the dry crude product in a first column to yield a first residue comprising acetic acid and a first distillate comprising ethanol and ethyl acetate, wherein the dry crude product is directly fed to the first column from the adsorption unit; and
   separating at least a portion of the first distillate in a second column to yield a second distillate comprising ethyl acetate and a second residue comprising ethanol.

19. A process for producing ethanol, comprising the steps of:
   providing a crude ethanol product comprising ethanol, acetic acid, ethyl acetate, and water;
   removing a majority of the water in the crude ethanol product using an adsorption unit, one or more membranes, molecular sieves, or a combination thereof to form a water stream and a dry crude product, wherein the dry crude product comprises less than 5 wt. % water; and
   feeding the dry crude product directly to one or more distillation columns to recover ethanol therefrom.

20. The process of claim 19, wherein at least 90% of the water from the crude ethanol is removed.

* * * * *